US012622989B2

(12) United States Patent
Rao

(10) Patent No.: US 12,622,989 B2
(45) Date of Patent: May 12, 2026

(54) SYSTEM AND METHOD FOR STERILIZATION OF OBJECTS

(71) Applicant: PHARMALAB INDIA PVT. LTD.,
Maharashtra Mumbai (IN)

(72) Inventor: M. Nageswara Rao, Gandhinagar
Gujarat (IN)

(73) Assignee: PHARMALAB INDIA PVT. LTD.,
Maharashtra Mumbai (IN)

( * ) Notice: Subject to any disclaimer, the term of this
patent is extended or adjusted under 35
U.S.C. 154(b) by 0 days.

(21) Appl. No.: 18/733,316

(22) Filed: Jun. 4, 2024

(65) Prior Publication Data

US 2024/0325582 A1      Oct. 3, 2024

Related U.S. Application Data

(63) Continuation      of      application      No.
PCT/IN2022/050510, filed on Jun. 1, 2022.

(30) Foreign Application Priority Data

Feb. 7, 2022      (IN) .............................. 202221006538

(51) Int. Cl.
*A61L 2/208*      (2026.01)
*A61L 2/10*      (2026.01)
(Continued)

(52) U.S. Cl.
CPC ................. *A61L 2/208* (2013.01); *A61L 2/10*
(2013.01); *A61L 2/26* (2013.01); *B01D 53/268*
(2013.01);
(Continued)

(58) Field of Classification Search
CPC ... A61L 2/208; A61L 2/10; A61L 2/26; A61L
2202/11; A61L 2202/15; A61L 2/24;
(Continued)

(56) References Cited

U.S. PATENT DOCUMENTS 4,744,951 A      5/1988  Cummings et al.
6,077,480 A  *  6/2000  Edwards ................... A61L 2/24
422/298
(Continued)

FOREIGN PATENT DOCUMENTS

CN      205832225 U      12/2016
EP      0991434 A1      4/2000
(Continued)

OTHER PUBLICATIONS

Dincer, "Comprehensive Energy Systems", Energy Systems (Year: 2018).*

(Continued)

*Primary Examiner* — Brendan A Hensel
(74) *Attorney, Agent, or Firm* — Schwegman Lundberg &
Woessner, P.A.

(57)      ABSTRACT

The present subject matter relates to a system and a method
for producing Hydrogen Peroxide in situ for sterilization of
objects. In the system and the method, Hydrogen Peroxide
solution of 30-35% concentration is processed to reach a
target concentration value in a range of 90-95% of the
resulting concentrated Hydrogen Peroxide.

10 Claims, 3 Drawing Sheets

(51) Int. Cl.
 *A61L 2/26* (2006.01)
 *B01D 53/26* (2006.01)

(52) U.S. Cl.
 CPC ........ *A61L 2202/11* (2013.01); *A61L 2202/15* (2013.01); *B01D 2257/80* (2013.01)

(58) Field of Classification Search
 CPC ..... A61L 2/28; B01D 53/268; B01D 2257/80; C01B 15/013
 See application file for complete search history.

(56) References Cited

U.S. PATENT DOCUMENTS

| | | | |
|---|---|---|---|
| 6,656,424 B1 | 12/2003 | Deal | |
| 2002/0014207 A1* | 2/2002 | Sivaramakrishnan .. | B01F 23/12 |
| | | | 118/715 |
| 2003/0053930 A1* | 3/2003 | Hui ........................... | A61L 2/26 |
| | | | 422/292 |
| 2005/0095168 A1 | 5/2005 | Centanni et al. | |
| 2008/0038166 A1* | 2/2008 | Hill ......................... | A61L 2/208 |
| | | | 422/292 |
| 2008/0219884 A1* | 9/2008 | Berentsveig .............. | A61L 2/24 |
| | | | 422/33 |
| 2009/0185960 A1* | 7/2009 | Busujima .................. | A61L 2/24 |
| | | | 422/186.3 |
| 2012/0244261 A1* | 9/2012 | Harvey .................... | A23B 4/26 |
| | | | 426/332 |
| 2013/0302207 A1 | 11/2013 | Ahiska | |
| 2014/0116961 A1* | 5/2014 | Bokermann ........... | H05B 41/36 |
| | | | 210/748.11 |
| 2016/0008498 A1 | 1/2016 | Boysset et al. | |
| 2022/0096678 A1* | 3/2022 | Kea ........................... | A61L 2/10 |

FOREIGN PATENT DOCUMENTS

| | | | |
|---|---|---|---|
| EP | 1308173 A1 | | 5/2003 |
| EP | 1912552 B1 | | 9/2011 |
| GB | 546530 A | | 7/1942 |
| JP | 2012034781 A | * | 2/2012 |
| KR | 101424179 B1 | | 8/2014 |
| KR | 20150009104 | | 1/2015 |
| WO | WO-2023148750 A1 | | 8/2023 |

OTHER PUBLICATIONS

"India Application No. 202221006538, Examination report under sections 12 & 13 of the Patents Act, dated Jun. 8, 2022", (Jun. 8, 2022), 6 pgs.

"India Application No. 202221006538, Hearing Notice dated Nov. 2, 2022", (Nov. 2, 2022), 3 pgs.

"International Application No. PCT/IN2022/050510, International Search Report and Written Opinion mailed Oct. 10, 2022", (Oct. 10, 2022), 11 pgs.

"United Kingdom Application GB2405412.4, Examination Report Under Section 18(3) dated May 2, 2024", (May 2, 2024), 2 pgs.

"European Application No. 22738746.1, Office Action dated Apr. 9, 2025", (Apr. 9, 2025), 5 pgs.

* cited by examiner

302 — PLACE OBJECTS INSIDE VACUUM CHAMBER

304 — REGULATE SUPPLY OF HYDROGEN PEROXIDE SOLUTION

306 — REGULATE VAPORIZATION OF HYDROGEN PEROXIDE SOLUTION

308 — REGULATE PURGING PROCEDURE TO REACH TARGET CONCENTRATION VALUE IN RANGE OF 90-95% OF HYDROGEN PEROXIDE SOLUTION

310 — RECEIVE CONCENTRATED HYDROGEN PEROXIDE SOLUTION IN VACUUM CHAMBER

SYSTEM AND METHOD FOR STERILIZATION OF OBJECTS

PRIORITY CLAIM TO RELATED APPLICATIONS

This application is a continuation of International Application No. PCT/IN2022/050510, filed on 1 Jun. 2022, and published as WO2023/148750 on 10 Aug. 2023, which claims the benefit under 35 U.S.C. 119 to India application Ser. No. 202221006538, filed on 7 Feb. 2022, the benefit of priority of each of which is claimed herein, and which applications and publication are hereby incorporated herein by reference in their entirety.

BACKGROUND

In general, re-usable medical devices such as certain surgical instruments, endoscopes, etc., may be sterilized with a principal sterilizing agent to destroy or eliminate all forms of microbial life before re-use in order to minimize the likelihood that a contaminated device might be used on a patient, which could cause an infection in the patient.

BRIEF DESCRIPTION OF THE DRAWINGS

The following detailed description references the drawings, wherein.

DETAILED DESCRIPTION

Figure 1:
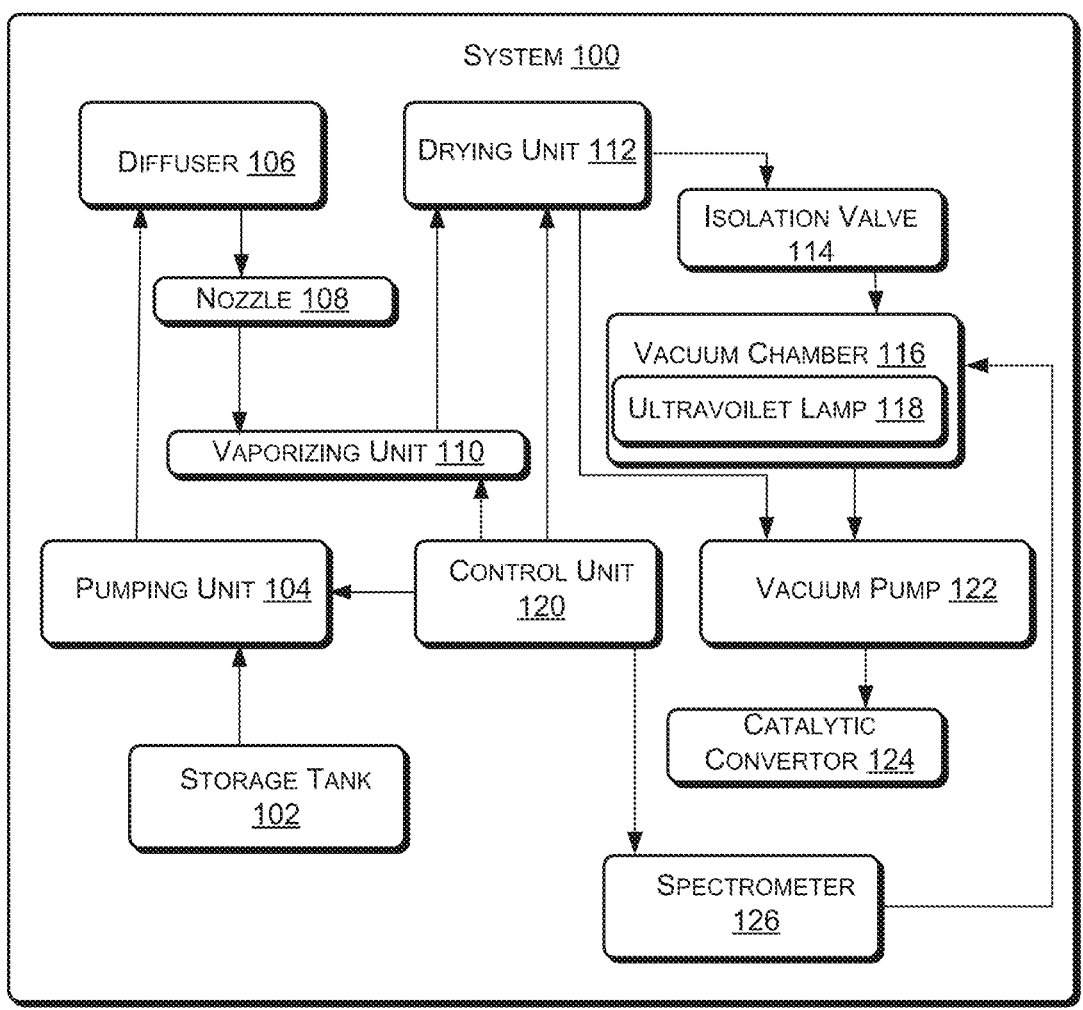
FIG. 1 shows a block diagram of a system for producing Hydrogen Peroxide in situ for sterilization of objects, according to an example.

Re-usable medical devices such as certain surgical instruments, may be sterilized using a vaporised hydrogen peroxide sterilization. The vaporised hydrogen peroxide sterilization is a low temperature sterilization generally used to sterilize heat-sensitive devices, such as medical devices. The sterilization is done before re-use to ensure that a contaminated device is not used on a patient. In the hydrogen peroxide sterilization, vapor of hydrogen peroxide is filled in a sterilizing chamber, where the medical devices to be sterilized are placed. Further, exposed surfaces of the medical devices contact the vapors of the hydrogen peroxide for the sterilization. After completing the hydrogen peroxide sterilization, the vapors are evacuated from the sterilizing chamber and converted to water and oxygen molecules.

Liquid hydrogen peroxide is flammable and can explode in case of any accident during the transportation from one location to another. Handling of highly concentrated liquid hydrogen peroxide is hazardous and cause injuries if the highly concentrated liquid hydrogen peroxide comes in contact with humans or animals. Therefore, highly concentrated hydrogen peroxide is not possible to be transported and handled directly for use in the sterilization processes.

Commonly, for the hydrogen peroxide sterilization, the hydrogen peroxide used is an aqueous solution having a concentration of 30-35% of the hydrogen peroxide. However, use of such a low concentration of 30-35% of the hydrogen peroxide results in high consumption of the hydrogen peroxide solution. Also, the duration of the hydrogen peroxide sterilization with such a concentration of the hydrogen peroxide solution may take several hours.

The present subject matter describes example systems and methods for producing Hydrogen Peroxide in situ for sterilization of objects. In the example systems and methods described herein, ultra-pure vapor of hydrogen peroxide of high concentration can be obtained.

To perform a hydrogen peroxide sterilization of an object, particularly, a medical device, the object is placed inside a vacuum chamber. In an example, the medical device may be a scalpel, a flow probe, an endoscope, etc. In an example, multiple medical devices may be placed inside the vacuum chamber. After placing the object inside the vacuum chamber, a pumping unit supplies a Hydrogen Peroxide solution of 30-35% concentration at a prespecified pressure and a prespecified rate to a vaporizing unit, which is connected to the pumping unit. Further, aqueous content of the pressurized Hydrogen Peroxide solution is vaporized to fine water vapors by the vaporizing unit. The fine water vapors of the Hydrogen Peroxide solution flow to a drying unit connected to the vaporizing unit. The fine water vapors enable convenient flow to the Hydrogen Peroxide solution without blocking the path. Further, a purging procedure is performed on the vaporized Hydrogen Peroxide solution. The purging procedure is performed by the drying unit to extract water vapors from the vaporized Hydrogen Peroxide solution. The drying unit is connected to the vaporizing unit. The water vapors are extracted until the resulting concentrated Hydrogen Peroxide have reached a target concentration value in a range of 90-95%. The concentrated Hydrogen Peroxide having the target concentration value in the range of 90-95% is received by the vacuum chamber, in which the objects to be sterilized are placed, for the sterilizing the objects.

Further, the pumping unit, the vaporizing unit, and the drying unit are connected to a control unit, which regulates each of the pumping unit, the vaporizing unit, and the drying unit. In an example, the control unit regulates the pumping unit to supply the Hydrogen Peroxide solution at the prespecified pressure and the prespecified flow rate. In an example, the control unit regulates the vaporizing unit to vaporize the aqueous content of the Hydrogen Peroxide solution into fine water vapors. In an example, the control unit regulates the drying unit to perform the purging procedure on the input volume of the vaporized Hydrogen Peroxide solution to obtain the concentrated Hydrogen Peroxide having the target concentration value in the range of 90-95%.

The vaporized Hydrogen Peroxide solution avoids inconsistency of flow and contamination of the hydrogen peroxide. Before entering the vacuum chamber, the hydrogen peroxide solution is free of humidity. Also, gases, particles and water vapors are separated from the Hydrogen Peroxide solution entering to the vacuum chamber. The concentrated Hydrogen Peroxide having the target concentration value in the range of 90-95% is ultra-pure and ensures efficient sterilization of the objects placed inside the vacuum chamber in a quick time. The high concentration of the Hydrogen Peroxide is produced in situ using the Hydrogen Peroxide solution of 30-35% concentration, thus such a high concentration does not cause any injury to a user carrying out the hydrogen peroxide sterilization.

These and other advantages of the present subject matter would be described in a greater detail in conjunction with the FIGS. 1-2 in the following description. The manner in which the machine tool is implemented and used shall be explained in detail with respect to the FIGS. 1-2.

It should be noted that the description merely illustrates the principles of the present subject matter. It will thus be appreciated that those skilled in the art will be able to devise various arrangements that, although not explicitly described herein, embody the principles of the present subject matter and are included within its scope. Furthermore, all examples recited herein are intended only to aid the reader in understanding the principles of the present subject matter. Moreover, all statements herein reciting principles, aspects and implementations of the present subject matter, as well as specific examples thereof, are intended to encompass equivalents thereof.

The following detailed description refers to the accompanying drawings. Wherever possible, the same reference numbers are used in the drawings and the following description to refer to the same or similar parts. While several examples are described in the description, modifications, adaptations, and other implementations are possible. Accordingly, the following detailed description does not limit the disclosed examples. Instead, the proper scope of the disclosed examples may be defined by the appended claims.

Figure 2:
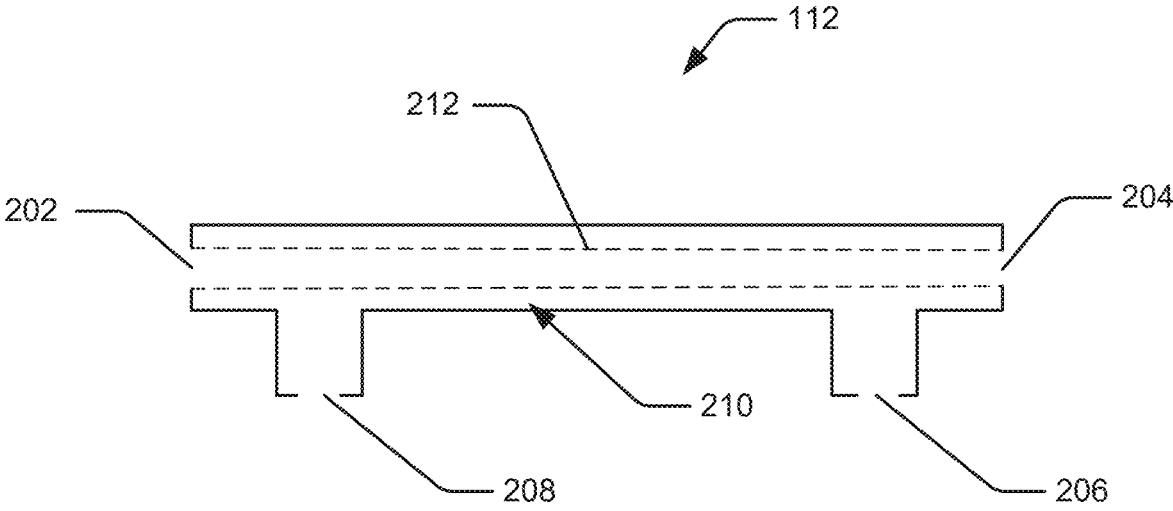
FIG. 2 shows a schematic diagram of a drying unit, according to an example.

FIG. 1 shows a block diagram of a system 100 for producing Hydrogen Peroxide in situ for sterilization of objects, according to an example. The system 100 is used for sterilization of objects, particularly re-usable medical devices using Hydrogen Peroxide and ultraviolet radiations. Example of medical devices include, but is not limited to, endoscopes, scalpels, catheters, medical implants, etc. The system 100 can be used in healthcare, semiconductor, pharma, hygienic sterilization, decontamination and plasma etching and other similar process. The system 100 includes a storage tank 102. The storage tank 102 may be a tank that can store a fluid, for example, Hydrogen Peroxide solution. The storage tank 102 can store a Hydrogen Peroxide solution of concentration in a range of 30-35%. The storage tank 102 may have any shape and can be made of a material that can withstand chemical properties of the Hydrogen Peroxide solution.

The system 100 further includes a pumping unit 104 having a first inlet (not shown) and a first outlet (not shown). The pumping unit 104 is a pump that can dispense an accurate volume of the Hydrogen Peroxide solution with a prespecified flow rate and a prespecified pressure. The first inlet of the pumping unit 104 is connected to the storage tank 102 to intake the stored Hydrogen Peroxide solution from the storage tank 102. In an example, the pumping unit 104 is a solenoid driven diaphragm pump which can dispense an accurate volume of 15 microliters of the Hydrogen Peroxide solution per stroke. In an example, the volume of the Hydrogen Peroxide solution to be dispensed by the pumping unit 104 can be adjusted between approximately 5 and 17 microliters thus allowing the pumping unit 104 to be calibrated to fit the parameters for the sterilization of any quantity of the objects. The pumping unit 104 can be operated between 0-20 Hz. The pumping unit 104 is self-priming and is capable of pumping both liquids and gases. The pumping unit 104 has high repeatability and has stable pumping characteristics over the entire lifetime. In an example, the pumping unit 104 has a maximum operating pressure 1 bar.

The system 100 further includes a diffuser 106 having a second inlet (not shown) and a second outlet (not shown). The diffuser 106 is to uniformly maintain the flow of the Hydrogen Peroxide solution in the system 100. The second inlet of the diffuser 106 is connected to the first outlet of the pumping unit 104 to receive the pressurized Hydrogen Peroxide solution from the pumping unit 104. The diffuser 106 further diffuses the pressurized Hydrogen Peroxide solution via the second outlet in such a manner that the liquid particle formation of the pressurized Hydrogen Peroxide solution must take place slowly and gradually. In an example, the diffuser 106 may be a porous metal diffuser. The porous metal diffuser maintains a laminar flow of the pressurized Hydrogen Peroxide solution. Such a laminar flow results in a minimal displacement of the particles in the pressurized Hydrogen Peroxide solution during the sterilization. The diffuser 106 includes a diffuser element (not shown) made of sintered stainless steel or nickel membrane filter. In an example, a housing (not shown) of the diffuser 106 may be made of 316 L stainless steel. The diffuser 106 may operate at a maximum operating temperature of 100 degree Celsius. In an example, the diffuser 106 may diffuse the pressurized Hydrogen Peroxide solution with a maximum differential pressure of 4 bar.

The system 100 further includes a nozzle 108 having a third inlet (not shown) and a third outlet (not shown). The third inlet of the nozzle 108 is connected with the second outlet of the diffuser 106. The third inlet of the nozzle 108 receives the diffused Hydrogen Peroxide solution from the diffuser 106 and then converts the the diffused Hydrogen Peroxide solution to atomized spray. In an example, the nozzle 108 is a misting nozzle for atomized spray of the diffused Hydrogen Peroxide solution with uniform droplet size, consistent spray angles, and at lower pressures. The misting nozzle may include an integrated filter (not shown) to minimize clogging of the misting nozzle. Thereby, maximizing the life of the misting nozzle. In an example, the misting nozzle may be made of stainless steel 316. In an example, the misting nozzle may generate a maximum flow of 1000 millilitres per hour and a maximum pressure of 3 bar. The misting nozzle is characterized by their very small droplet size and relatively small flow rate. The pressure of the incoming Hydrogen Peroxide solution is used to drive the atomization process. Higher pressure of the incoming Hydrogen Peroxide solution produces increasingly finer droplets.

In an example, the nozzle 108 may be an ultrasonic nozzle. The ultrasonic nozzle is operated by converting high frequency sound waves into mechanical energy that is transferred into a liquid, creating standing waves. As the liquid exits the atomizing surface of the ultrasonic nozzle, it is broken into a fine mist of uniform micron sized droplets. Unlike the misting nozzle, the ultrasonic nozzle does not force the Hydrogen Peroxide solution through a small orifice using the high pressure in order to produce a spray. In the ultrasonic nozzle, the Hydrogen Peroxide solution is fed, without pressure, through a center of the ultrasonic nozzle with a relatively large orifice and is atomized due to ultrasonic vibrations in the ultrasonic nozzle. The power required to operate the ultrasonic nozzle is between 1 and 8 Watts.

The system 100 further includes a vaporizing unit 110 having a fourth inlet (not shown) and a fourth outlet (not shown). The fourth inlet of the vaporizing unit 110 is connected to the third outlet of the nozzle 108. The vaporizing unit 110 is to vaporize the atomized spray of the Hydrogen Peroxide solution received from the nozzle 108. The vaporizing unit 110 may include a flow control valve (not shown) and a vaporization chamber (not shown). The flow control valve controls the flow of the atomized spray of the Hydrogen Peroxide solution received at the fourth inlet of the vaporizing unit 110 so that a desired amount of the Hydrogen Peroxide solution is dispended to the vaporization chamber. In the vaporization chamber, the atomized spray of the Hydrogen Peroxide solution dispended from the flow control valve is converted into vapors. The vapors of the Hydrogen Peroxide solution do not form scales inside inner surfaces of the system, which would have otherwise formed, and the system may be chocked due to such scales. The vaporizing unit 110 is configured to operate at a maximum operating temperature of 150 degree Celsius. The vaporizing unit 110 has a wetted surface made of 316 L stainless steel. The vaporizing unit 110 may include a piezo control valve to control the vapor dispense from the vaporizing unit 110. The vaporizing unit 110 may generate a maximum flow rate of 0.5 cubic centimetres per minute. The vaporizing unit 110 of the system 100 is formed to measure either the Hydrogen Peroxide solution before or the vapor after the vapor conversion by a mass flow rate, so that the rate is not affected by pressure or temperature changes.

The system 100 further includes a drying unit 112 having a fifth inlet (not shown in FIG. 1) and a fifth outlet (not shown in FIG. 1). The drying unit 112 is explained in detail in FIG. 2. FIG. 2 shows a schematic diagram of the drying unit 110, according to an example. The fifth inlet 202 and the fifth outlet 204 of the drying unit 112 are shown in FIG. 2. The fifth inlet 202 of the drying unit 112 is connected to the fourth outlet of the vaporizing unit 110 to receive the Hydrogen Peroxide solution in vaporized form. Further, the drying unit 112 includes a purge gas inlet 206 and a purge gas outlet 208. The purge gas inlet 206 is disposed distal to the fifth inlet 202 to receive a dry purge gas. The dry purge gas gets passthrough annular section 210 of the outer wall of an inner membrane nano tube 212 with the vaporized form of the Hydrogen Peroxide solution so that the aqueous content of the Hydrogen Peroxide solution is absorbed by the dry purge gas through the membrane wall. After absorbing the aqueous content, the purge gas becomes wet, and the Hydrogen Peroxide reaches up to a target concentration value of 90-95%. The purge gas outlet 208 is disposed proximal to the fifth inlet 202 to output the wet purge gas after the purging procedure. Further, the fifth outlet 204 is to output the dried and concentrated Hydrogen Peroxide after the purging procedure. In an example, the drying unit 112 is a Nafion vapor dryer.

Returning to FIG. 1, the system 100 includes an isolation valve 114 and a vacuum chamber 116 having a sixth inlet (not shown) and a sixth outlet (not shown). The isolation valve 114 is disposed between the drying unit 112 and the vacuum chamber 116 for isolating the drying unit 112 from the vacuum chamber 116 so that the dried and concentrated Hydrogen Peroxide can flow into the vacuum chamber 116 as per the requirement.

The sixth inlet of the vacuum chamber 116 is connected to the drying unit via the isolation valve 114 to receive the dried and concentrated Hydrogen Peroxide. In an example, the vacuum chamber 116 is made of 316 L Stainless Steel or Aluminum. The vacuum chamber 116 includes an inner surface (not shown) having a surface finish of 0.4 micrometres. The surface finish of 0.4 micrometres is equivalent to mirror finish. In one example, the vacuum chamber 116 may include a single door, which is openable to place the objects for the sterilization and to remove the sterilized objects. In one example, the vacuum chamber 116 may include double doors, which are openable to place the objects for the sterilization and to remove the sterilized objects. In one example, the vacuum chamber 116 has a volume in a range of 40 to 1000 litres. The door of the vacuum chamber 116 is one of a slidably operated door, a hinge operated door, and a magnetic cylinder operated door.

In an example, the vacuum chamber 116 includes an ultraviolet lamp 118 disposed inside the vacuum chamber 116. The ultraviolet lamp 118 is to emit high energy cold ultraviolet radiations. Such high energy cold ultraviolet radiations are for drying water films deposited on inner surfaces of the vacuum chamber 116 and for breaking the residual molecules of the Hydrogen Peroxide, which are not broken by vacuum inside the vacuum chamber. In addition, the high energy cold ultraviolet radiations are for sterilizing cavities of the objects where the Hydrogen Peroxide is not reachable. Therefore, the objects are completely sterilized due to the combination of the highly concentrated Hydrogen Peroxide and the high energy cold ultraviolet radiations. The high energy cold ultraviolet radiations in the vacuum at 185 nm (approximately 6.7 eV), which corresponds to the resonant frequency of $H_2O$, is used to quickly dissolve the molecular bonds on the substrate, after which the free gaseous molecules can be extracted. Such a process is highly efficient due to the extremely high photon yield of the sources composed of a special synthetic quartz glass.

The system 100 further includes a control unit 120 connected to the pumping unit 104, the vaporizing unit 110, and the drying unit 112. The control unit 120 regulates respective operations of the pumping unit 104, the vaporizing unit 110, and the drying unit 112 simultaneously for producing the concentrated Hydrogen Peroxide with the target concentration value in the range of 90-95%. For example, the control unit 120 regulates the pumping unit 104 to supply the Hydrogen Peroxide solution at the prespecified pressure and the prespecified rate. Further, the control unit 120 regulates the vaporizing unit 110 to vaporize the aqueous content of the Hydrogen Peroxide solution into fine water vapors. The control unit 120 further regulates the drying unit 112 to perform the purging procedure on the input volume of the vaporized Hydrogen Peroxide solution to obtain the concentrated Hydrogen Peroxide having the target concentration value in the range of 90-95%.

The control unit 120 may include a processing resource. The processing resource may include microprocessors, microcomputers, microcontrollers, digital signal processors, central processing units, state machines, logic circuitries, and/or any other devices that manipulate signals and data based on computer-readable instructions. Further, functions of the various elements shown in the figures, including any functional blocks labelled as "processor(s)", may be provided through the use of dedicated hardware as well as hardware capable of executing computer-readable instructions.

The system 100 further includes a vacuum pump 122 connected to the vacuum chamber 116 and the drying unit 112. The vacuum pump 122 is connected to the sixth outlet of the vacuum chamber 116 so that when the sterilization is complete, the vacuum pump 122 operates to evacuate hydrogen peroxide vapors from the vacuum chamber 116 and venting out from an outlet of the vacuum pump 122 connected to a catalytic converter 124 to avoid any residual hydrogen peroxide particles. In addition, the vacuum pump 122 is connected to the purge gas outlet (not shown in FIG. 1) of the drying unit 112.

Further, the system 100 includes a spectrometer 126. The spectrometer 126 is used to separate and measure spectral components of a physical phenomenon, for example, sterilization of the objects in the system 100. The spectrometer 126 is connected to the control unit 120 and the ultraviolet lamp 118, to monitor the sterilization of the objects in the vacuum chamber 116 using the ultraviolet radiations inside the vacuum chamber 116. In an example, the spectrometer 126 is one of a HR4000 Composite-grating Spectrometer and a 200-1100 nm High Resolution Spectrometer. The spectrometer 126 may be connected to a spectroscopy software with a graphical user interface to view and control the complete sterilization process by analyzing the water vapors and Hydrogen Peroxide concentration inside the vacuum chamber 116. The spectrometer 126 can efficiently monitor all kinds of gases and vapors before and after the cleaning or cold sterilization process.

In an example, data, such as that related to the analysis of the water vapors and the Hydrogen Peroxide concentration may be stored in a storage device (not shown) coupled to the control unit 120. The storage device may include any non-transitory computer-readable medium including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. The storage device may store an activity data. In an example, the activity data includes the Hydrogen Peroxide concentration inside the vacuum chamber 116.

In an example, the system 100 includes interface(s) (not shown). The interface(s) may include a variety of interfaces, for example, interface(s) for users. The interface(s) may include data output devices. The interface(s) may facilitate the communication of the system 100 with various communication and electronic devices. In an example, the interface (s) may enable wireless communications between the system 100 and one or more other computing devices (not shown).

In case the objects placed inside the vacuum chamber 116 are identified as non-sterilized by the control unit 120 based on the monitoring by the spectrometer 126, the control unit is to further regulate the pumping unit 104, the vaporizing unit 110, and the drying unit 112 for adequately sterilizing the non-sterilized objects.

In an example, the system 100 may include a vacuum degasser (not shown) disposed between the pumping unit 104 and the diffuser 106. The vacuum degasser removes the dissolved gases from the Hydrogen Peroxide solution by applying vacuum to a semi-permeable membrane. For this, the Hydrogen Peroxide solution flows through a short length of a Teflon capillary inside a sealed chamber of the vacuum degasser. The sealed chamber is completely sealed to the environment and vacuum is applied with a pump (not shown). In an example, the pump may be a vacuum pump. Due to this vacuum any dissolved gases in the Hydrogen Peroxide solution running through the Teflon capillary are removed through its semi-permeable membrane wall. The high efficiency of the Teflon material allows the usage of a very short length of capillary inside the sealed chamber.

In an example, the system 100 may include a filter (not shown) the pumping unit 104 and the drying unit 112 for separating solid impurities from the Hydrogen Peroxide solution. In an example, the filter is disposed between the pumping unit 104 and the diffuser 106. The filter may filter impurities of 0.1 to 5 microns.

During operation of the system 100, when the control unit 120 determines that the objects, such as medical devices, to be sterilized are placed inside the vacuum chamber 116, the control unit 120 regulates the supply of the Hydrogen Peroxide solution of 30-35% concentration at the prespecified pressure and the prespecified flow rate from the pumping unit 104 to the vaporizing unit 110. During the supply of the Hydrogen Peroxide solution of 30-35% concentration from the pumping unit 104 to the vaporizing unit 110, the Hydrogen Peroxide solution is diffused by the diffuser 106 and further an atomized spray of the Hydrogen Peroxide solution having a uniform droplet size is generated by the nozzle 108. The control unit 120 further regulates the vaporization of the received atomized spray of the Hydrogen Peroxide solution by the vaporizing unit for vaporizing aqueous content of the Hydrogen Peroxide solution into fine water vapors. Further, the control unit 120 regulates the purging procedure by the drying unit 112 on an input volume of the vaporized Hydrogen Peroxide solution to extract the water vapors therefrom until the resulting concentrated Hydrogen Peroxide have reached the target concentration value in the range of 90-95%. Further, the vacuum chamber 116 receives the concentrated Hydrogen Peroxide from the drying unit 112 via the isolation valve 114 for sterilizing the objects placed inside the vacuum chamber 116. In addition, the ultraviolet lamp 118 emitting high energy cold ultraviolet radiations dries the water films deposited on inner surfaces of the vacuum chamber, sterilizes cavities of the objects where the Hydrogen Peroxide is not reachable, and breaks the residual molecules of the Hydrogen Peroxide, which are not broken by vacuum inside the vacuum chamber. While sterilizing the objects placed inside the vacuum chamber 116, the vacuum chamber 116 is monitored by the spectrometer 126 and monitoring data is communicated to the control unit 120. In case the objects are identified as non-sterilized by the control unit 120 based on the monitoring, the control unit 120 is to further regulate the pumping unit 104, the vaporizing unit 110, and the drying unit 112 for efficiently sterilizing the objects placed inside the vacuum chamber 116.

Figure 3:
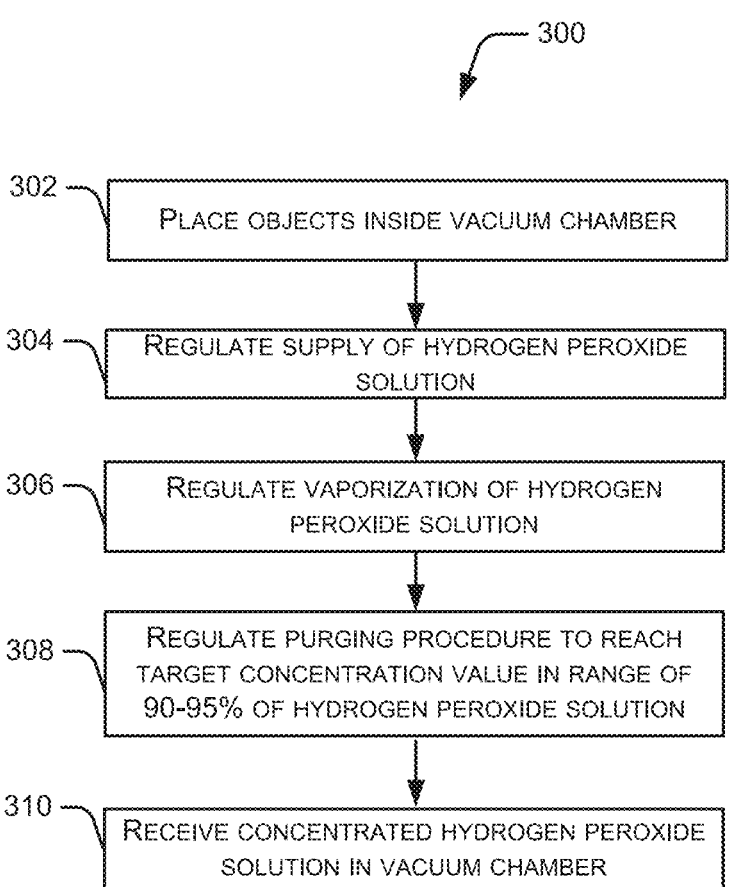
FIG. 3 shows a flow diagram of a method for producing Hydrogen Peroxide in situ for sterilization of objects, according to an example.

FIG. 3 shows a flow diagram of a method 300 for producing Hydrogen Peroxide in situ for sterilization of objects, according to an example. The order in which the method 300 is described is not intended to be construed as a limitation, and any number of the described steps may be combined in any order to implement the method 300, or an alternative method. Further, certain steps have been omitted in the flow diagram for the sake of brevity and clarity. It may be noted that the method 300 is described with respect to the system 100.

Referring to FIG. 3, at step 302, the objects are placed inside the vacuum chamber 116 by opening the door of the vacuum chamber 116. In an example, the objects are medical devices, such as endoscopes. In an example, the objects may be manually placed inside the vacuum chamber 116. In an example, the objects may be placed inside the vacuum chamber 116 using a robotic arm. After placing the objects inside the vacuum chamber 116, the door of the vacuum chamber 116 is closed either manually or electronically.

At step 304, a supply of a Hydrogen Peroxide solution of 30-35% concentration from the pumping unit 104 is regulated by the control unit 120. The control unit 120 regulates the pumping unit 104 such that the Hydrogen Peroxide solution is further supplied at a prespecified pressure and a prespecified rate from the pumping unit 104 to the vaporizing unit 110.

At step 306, the control unit 120 regulates the purging procedure by the drying unit 112 on an input volume of the vaporized Hydrogen Peroxide solution to extract the water vapors therefrom until the resulting concentrated Hydrogen Peroxide have reached the target concentration value in the range of 90-95%. Such a high concentration of the Hydrogen Peroxide is difficult to use if transported from other location to the sterilization location.

At step 308, the concentrated Hydrogen Peroxide is received in the vacuum chamber. After receiving the concentrated Hydrogen Peroxide, the objects placed inside the vacuum chamber are sterilized using the concentrated Hydrogen Peroxide.

Although implementations for the system 100 and the method are described, it is to be understood that the present subject matter is not necessarily limited to the specific features described. Rather, the specific features are disclosed as implementations.

I claim:

1. A system for producing Hydrogen Peroxide in situ for sterilization of objects, the system comprising:

a pumping unit, at a first end of the system, to supply a Hydrogen Peroxide solution of 30-35% concentration at a prespecified pressure and a prespecified rate;

a vaporizing unit, fluidically connected to the pumping unit, to receive the Hydrogen Peroxide solution and vaporize the pressurized Hydrogen Peroxide solution;

a vacuum pump fluidically connected at a second end of the system thereby generating a negative vacuum pressure between the vaporizing unit and the vacuum pump, a drying unit, fluidically connected between the vaporizing unit and the vacuum pump to perform a dry purging procedure on the vaporized Hydrogen Peroxide solution, the drying unit comprising:

a fifth inlet connected to the vaporizing unit to receive the vaporized Hydrogen Peroxide solution, an inner membrane tube defining a first flow path for the vaporized Hydrogen Peroxide solution, an annular purge-gas passage surrounding the inner membrane tube the annular passage having:

a purge-gas inlet disposed distal to the fifth inlet to receive a dry purge gas, and a purge-gas outlet disposed proximal to the fifth inlet to discharge a wet purge gas, wherein, at least under the effect of the negative vacuum pressure generated by the vacuum pump, the inner membrane tube is to cause water vapor to diffuse therethrough into the annular passage while vaporized Hydrogen-Peroxide is retained within the inner membrane tube; and a fifth outlet fluidically connecting the drying unit to the vacuum chamber to output concentrated Hydrogen Peroxide vapors substantially devoid of water vapor from the inner membrane tube; and a vacuum chamber, fluidically connected between the drying unit and the vacuum pump, to receive the concentrated Hydrogen Peroxide vapors for the sterilization of the objects, wherein the vacuum pump is to cause movement of the Hydrogen Peroxide vapors at least from the vaporizing unit to the vacuum chamber, and wherein the system further comprises a degasser that removes the dissolved gases from the Hydrogen Peroxide solution by applying vacuum to a semi-permeable membrane, the degasser is fluidically connected between the pumping unit and the vacuum pump such that the Hydrogen Peroxide vapors received at the vacuum chamber are substantially devoid of gases, wherein the Hydrogen Peroxide is generated in situ.

2. The system as claimed in claim 1, wherein the system comprises a control unit connected to the pumping unit, the vaporizing unit, and the drying unit, wherein the control unit is to:

regulate the pumping unit to supply the Hydrogen Peroxide solution at the prespecified pressure and the prespecified rate;

regulate the vaporizing unit to vaporize an aqueous content of the Hydrogen Peroxide solution into water vapours; and regulate the drying unit to perform the dry purging procedure on the vaporized Hydrogen Peroxide solution to obtain the concentrated Hydrogen Peroxide vapors substantially devoid of water vapor.

3. The system as claimed in claim 2, wherein the system comprises an ultraviolet lamp disposed inside the vacuum chamber, wherein the ultraviolet lamp is to emit ultraviolet radiations for drying water films deposited on inner surfaces of the vacuum chamber, for sterilizing cavities of the objects where the Hydrogen Peroxide is not reachable, and for breaking the residual molecules of the Hydrogen Peroxide, which are not broken by vacuum inside the vacuum chamber.

4. The system as claimed in claim 1, wherein the pumping unit is a solenoid driven diaphragm pump.

5. The system as claimed in claim 1, wherein the system comprises a filter disposed between the pumping unit and the drying unit for separating impurities from the Hydrogen Peroxide solution.

6. The system as claimed in claim 1, wherein the system comprises a diffuser between the pumping unit and the vaporizing unit to diffuse the pressurized Hydrogen Peroxide solution received from the pumping unit.

7. The system as claimed in claim 6, wherein the system comprises a nozzle disposed between the diffuser and the vaporizing unit to generate an atomized spray of the Hydrogen Peroxide solution having a uniform droplet size.

8. The system as claimed in claim 7, wherein the nozzle is one of a misting nozzle and an ultrasonic nozzle.

9. The system as claimed in claim 3, wherein the inner surfaces of the vacuum chamber have a surface finish of 0.4 micrometers.

10. The system as claimed in claim 1, wherein the fluidic connection between the vacuum pump and the vaporizing unit is controlled by a piezoelectric valve.

*    *    *    *    *